United States Patent [19]

Columbus

[11] 4,050,451
[45] Sept. 27, 1977

[54] BLOOD COLLECTION AND SEPARATION DEVICE

[75] Inventor: Richard Lewis Columbus, Rochester, N.Y.

[73] Assignee: Eastman Kodak Company, Rochester, N.Y.

[21] Appl. No.: 714,433

[22] Filed: Aug. 13, 1976

[51] Int. Cl.² .............................................. A61B 5/10
[52] U.S. Cl. ............................. 128/2 F; 128/DIG. 5; 210/DIG. 23
[58] Field of Search ................. 128/2 F, DIG. 5, 276, 128/216; 210/314, 359, DIG. 23; 356/39, 40, 41, 42, 246

[56] References Cited

U.S. PATENT DOCUMENTS

| | | | |
|---|---|---|---|
| 3,814,079 | 6/1974 | LeRoy, Sr. | 128/2 F |
| 3,852,194 | 12/1974 | Zine, Jr. | 210/DIG. 23 |
| 3,926,521 | 12/1975 | Ginzel | 128/2 F X |
| 3,929,646 | 12/1975 | Adler | 210/359 |

Primary Examiner—John D. Yasko
Attorney, Agent, or Firm—Dana M. Schmidt

[57] ABSTRACT

A device is provided for collecting and separating a two-phase liquid, and comprises a collecting compartment containing a microporous filler where the liquid is deposited, so as to draw the liquid in by capillary action. The compartment is vented to the atmosphere.

19 Claims, 6 Drawing Figures

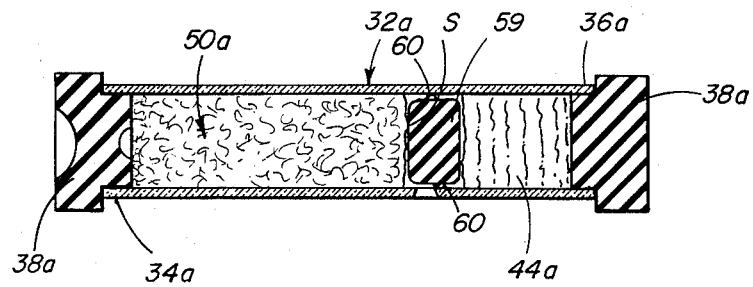
FIG. 4
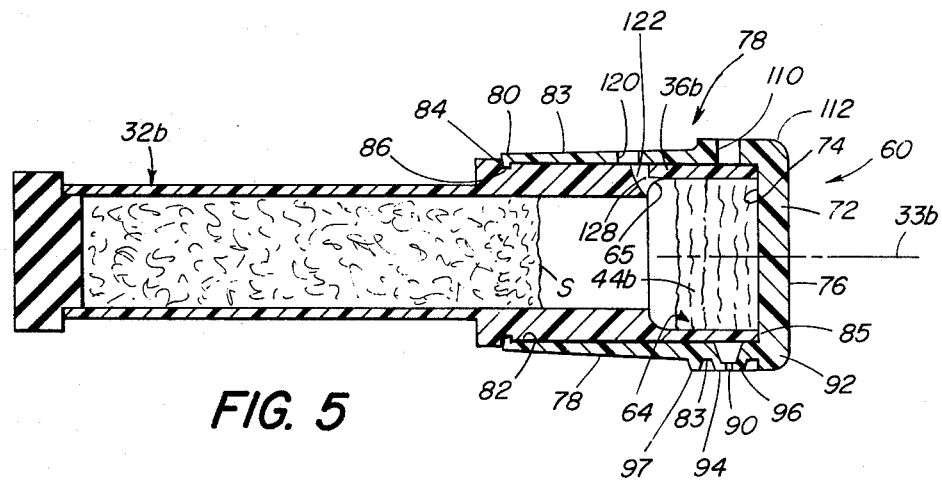
FIG. 5
FIG. 6

BLOOD COLLECTION AND SEPARATION DEVICE

BACKGROUND OF THE INVENTION

1. Field of the Invention

This invention relates to a device for the collection and separation of two-phase liquids such as blood. Optionally, the same device can be used to dispense the serum so separated.

2. State of the Prior Art

Of the many devices available to provide blood serum for analysis, the one which has become the norm is the evacuated container. This is simply a partially evacuated glass tube openable at one end except for a septum placed there. One particularly useful improvement of such an evacuated container comprises such a glass tube with a movable plug contained within the tube. The plug is preferably a silica gel, with or without a plastic cup-like mandrel positioned with its open end pointed to the septum. By reason of the vacuum, collected blood is easily drawn into the container. The container is then spun about a centrifuge axis adjacent to the septum end, and the gel by reason of its selected specific gravity works up to the serum-cell interface where it plugs the container against remixing of the serum and cells. An example of such a container without the mandrel is shown in U.S. Pat. No. 3,852,194.

Although such a device is useful in separating the serum from the cells, it has not avoided transfer difficulties after the serum is separated. That is, after centrifuging, the serum is commonly poured off into yet another container for the desired clinical testing. All such transfer operations are time consuming, requiring either hand processing or complicated, expensive automatic handling. Furthermore, whenever there is a transfer of a liquid sample to a separate, open container, the sample is aerated and $CO_2$ loss or gain can occur. There is also the danger of improper transfer, either by the use of the wrong container, by the improper patient labeling of the new container, or by both. Still further, contamination of the serum by foreign materials can occur, including, for example, contamination by blood cells collected at the septum-container interface prior to centrifuging, a condition known as "blood-ring contamination."

Still other drawbacks concerning evacuated containers are that the rapid intake tends to cause hemolysis by reason of the high shear rate, particularly when flow is through reduced diameters; the vacuum can cause collapse of the patient's vein; and occasionally the containers become "flat", i.e., they lose their vacuum. In such a case of a "flat" container, the broken seal is generally insufficient to create a truly vented configuration, so that the hydrostatic pressure of the veins from which the blood is drawn encounters back pressure, and the rate of fill is insufficient. When the container is formed from solid glass, it is not possible prior to actual use to determine the loss of vacuum merely by visual inspection, and the result is that the patient has to wait while the technician looks for a new container.

Evacuated containers have, in some instances, included inorganic fillers in the compartment that collects the blood sample. A mechanical phase separator causes the filler to collapse during centrifuging. U.S. Pat. No. 3,929,646 is illustrative of such a device. However, such filler is positioned therein solely to act as a blood-clotting agent, and must be only loosely packed to allow the gel portion of the phase separator to move through it. Because the draw of the blood is provided by the vacuum, there is no attempt to use the filler as a capillary assist. As a result, the filler does not overlap with the terminus of the cannula — that is, it is not in contact with the blood as it leaves the cannula. Instead, the filler extends from the cell-collecting portion of the compartment to a location falling far short of the mechanical phase separator and therefore, of the penetratable closure means or septum.

Flexible containers have been used to collect whole blood; and, by reason of their flexibility, they may have capillary passageways somewhere defined when the walls are collapsed. However, the collapsed wall condition is designed not to fill the containers by capillary action, but rather either to create a vacuum which causes filling of the container, as shown for example, in U.S. Pat. No. 3,513,829, or to indicate whether desired arterial blood as opposed to undesired venous blood is being collected, as shown for example in U.S. Pat. No. 3,785,367.

U.S. Pat. No. 3,867,923 is representative of blood collection bags which are completely collapsed along their entire length, and which therefore initially provide a capillary passageway along their entire length. However, such devices lose their effective capillary as soon as blood enters. Because they are not vented to the atmosphere, they require the patient's blood pressure to expend the device into its full volume. They cannot be used to collect non-pressurized blood.

Blood flow devices having capillary restrictions at a portion intermediate the ends thereof have been constructed not for the purpose of collecting blood and for separating serum, but rather for blood cell counting, as shown for example, in U.S. Pat. Nos. 2,369,577; 2,779,232; 2,807,416 and 2,875,666.

Patents disclosing a capillary passageway forming at least a part of a blood collection system include U.S. Pat. Nos. 3,645,252; 3,640,267; 3,898,982; and 3,926,521. However, these have not been suited for the use with venous collection, have been too reduced in capacity, and/or have lacked the optional capability of providing a dispensing of serum separated within the compartment.

Patents relating generally to the background of blood or other liquid collection include for example U.S. Pat. Nos. 3,513,829; 3,610,226; 3,814,079; 3,867,924; 3,897,340; 3,909,419; 3,920,557; 3,931,010; 3,938,957; 3,938,958; 3,452,601; 3,496,777; and 3,511,570.

RELATED APPLICATIONS

In U.S. application Ser. No. 644,014 filed on Dec. 24, 1975, entitled "Gas Pressure-Activated Drop Dispenser," a continuation-in-part application of Ser. No. 545,670, filed on Jan. 30, 1975, now abandoned there is disclosed a dispenser chamber uniquely designed to dispense microvolume drops, one at a time, of fluids of variable properties such as blood serum. In U.S. application Ser. No. 581,345, filed on May 27, 1975, a continuation-in-part of application Ser. No. 539,577, filed on Jan. 8, 1975, now abandoned entitled "Biological Fluid Dispenser and Separator", there is disclosed a combined serum separator and dispenser which preferably draws in blood at one end and collects and dispenses drops of serum at the other, whereby blood ring contamination can be avoided. The device can be vented or evacuated.

In commonly owned U.S. application Ser. No. 703,476 filed on July 8, 1976, a continuation-in-part of Ser. No. 609,121, filed on Aug. 29, 1975 by R. F. Jakubowicz, entitled "Telescoping Serum Separator and Dispenser" now abandoned, there is disclosed a combined serum separator and disperser wherein the dispensing chamber telescopes with respect to the serum separating compartment to open or close flow of serum from the separating compartment to the dispensing chamber.

In U.S. application Ser. No. 658,208, filed on Feb. 17, 1976 entitled "Vented Liquid Collection Device", there is disclosed a vented collecting and dispensing device which uses a capillary passageway along a portion of the sample collection length of the collection compartment to increase the speed of collection. The prime mover of the blood in such a device is the veinal pressure of the patient.

In U.S. application Ser. No. 674,462, filed on Apr. 7, 1976, entitled "Collection and Dispensing Device for Non-Pressurized Liquids", there is disclosed a vented collecting and dispensing device which uses a capillary passageway along the entire sample collection length of the compartment to provide a draw for non-pressurized liquid such as blood from a pin-prick.

OBJECTS OF THE INVENTION

It is an object of the invention to provide a vented blood collection and serum separation device with a capillary assist, capable of utilizing a simple cylindrical compartment.

It is a related object to provide such a device which is capable of dispensing serum separated within the device.

Other objects and advantages will become apparent upon reference to the following Summary and Description of the Preferred Embodiments, when read in light of the attached drawings.

SUMMARY OF THE INVENTION

The invention concerns a vented blood collection device suitable for serum separation, and optionally, for serum dispensing thereafter.

More specifically, according to one aspect of the invention, there is provided a vented liquid collection device for use with a liquid injector having a penetrating portion extending a predetermined penetrating length to an apertured tip, the device comprising an elongated compartment having opposite end portions, one of the end portions having a vent aperture extending to the exterior of the device; closure means in at least the other of the end portions for admitting a liquid injector and for closing the compartment; and a microporous filler confined within said compartment, the filler 1) filling the compartment at at least the point occupied by the apertured tip when inserted through the closure means; 2) being wettable by and inert to the liquid to be collected; and 3) being provided with open pores sufficiently small in diameter as to provide a capillary draw on liquid deposited therein by the injector.

In accordance with another aspect of the invention, the location of the filler at the vicinity of the apertured tip is achieved by extending the filler from a position adjacent to the closure means to a point removed therefrom by a distance that exceeds the predetermined penetrating length of the injector.

BRIEF DESCRIPTION OF THE DRAWINGS

FIGS. 4 and 5 are views similar to that of FIG. 2, less the cannula, wherein alternate embodiments are illustrated; and FIG. 6 is a view similar to that of FIG. 5, but showing the device in position to dispense serum.

DESCRIPTION OF THE PREFERRED EMBODIMENTS

The invention concerns a device particularly suited to the collection and separation of the phases of two-phase liquids such as blood. Although both of these functions are hereinafter discussed in detail, the invention is not limited to devices having both, but also covers devices of this type which provide just the collection function. Subsequent processing, such as phase separation, can be provided by pouring the collected liquid into a container designed for such processing. Similarly, dispensing of one of the phases following phase separation can be done in a separate container, or it can be done in a dispensing chamber which is a part of the collection device as disclosed herein.

Figure 1:
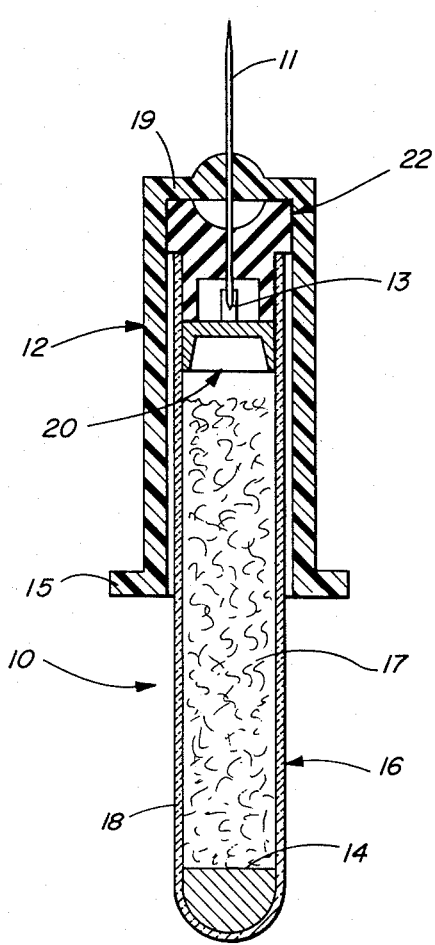
FIG. 1 is an elevational view in section of a blood collection and separation device constructed according to the prior art.

In FIG. 1 there is illustrated a prior art blood collection and serum separation device 10 of the evacuated type in conjunction with a standard cannula 11 and syringe 12. Blood is delivered to the device 10 from the penetrating, apertured tip 13 of the cannula. As is typical, the syringe is a tube open at one end 15 and closed at the other end 19, with the body of the cannula affixed to the closed end 19 and the apertured tip 13 proximal to the open end 15. Such a prior art device 10 is prepared by depositing a sealant 14 at the bottom of a tube 16, an inorganic filler 17 adjacent to the sealant also in the bottom portion 18 of tube 16, a mechanical phase separator or piston 20 at the top of the tube, and by drawing a vacuum prior to placing a septum or stopper 22 at the top of the tube. The apertured tip 13 of cannula 11 then penetrates septum 22 a predetermined length but only to a point short of the piston 20. The filler 17 is used solely to assist in clotting the blood. Because it is not located at the tip of the cannula, the filler cannot give a direct assist to the collection of blood via capillary action. No assist would normally be necessary in such an evacuated device.

A typical example of such a device is also shown in the aforementioned U.S. Pat. No. 3,929,646.

Figure 2:
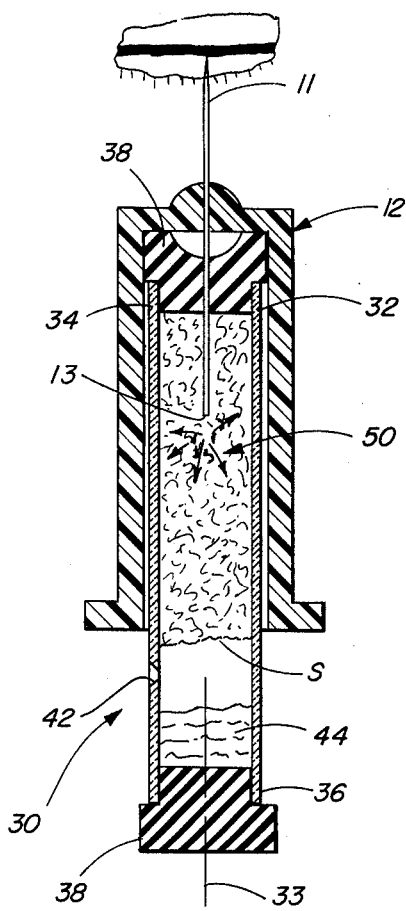
FIG. 2 is an elevational view similar to FIG. 1, but illustrating a device constructed in accordance with the invention.

In accordance with one aspect of the invention, the blood collection and separation device 20, FIG. 2, preferably comprises an open-ended elongated, preferably cylindrical tube 32, having a longitudinal axis 33 and opposite end portions 34 and 36, the function of the tube being to provide a blood collection and serum separation compartment. As used herein, "end portions" means those opposite portions adjacent the ends of the compartment, which are intended to confine cells separated from serum, respectively. A microporous filler 50 is positioned within the compartment so as to assist in drawing blood from injectors or cannulas used to fill it, and specifically, so as to fill the compartment at the point occupied by tip 13 of the cannula when the latter is in position to deliver blood. Closure means, such as septums 38 or their equivalent, are positioned in each end portion 34 and 36. As will be readily apparent, the septum in end portion 34 preferably is capable of penetration by a cannula 11. End portion 34 is initially filled with blood, and later becomes, during phase separation, the portion confining or containing the blood cells. Opposite end portion 36 confines and/or contains the serum resulting from phase separation. To provide venting of the compartment to the atmosphere, a vent aperture 42 is formed in tube 32, closer to end portion 36 than to end portion 34, and preferably not in contact with the filler. This vent is open during collection of the blood via the cannula 11 and syringe 12, which are substantially the same as in FIG. 1, and is closed during subsequent processing. As is apparent, tube 32 is slidable in syringe 12 so as to force the cannula through septum 38 to its full extent.

Also located adjacent end portion 36 prior to centrifuging is a movable phase separator 44. This separator preferably comprises a silica gel which can be a blend of hydrophobic silicon dioxide and a silicone, such as dimethylpolysiloxane, blended to give a thixotropic gel having a specific gravity between about 1.035 and 1.06, and preferably about 1.04–1.05, and a viscosity between about 400 and about 500 poise at a shear rate of about 500 sec.$^{-1}$, and typically 451 poise at 506 sec.$^{-1}$. The gel can be used by itself without a mandrel, as is taught for example in U.S. Pat. No. 3,852,194, or with a mandrel as manufactured for example by Corning Glass Works. The separator functions to maintain phase separation between separated blood cells and the serum, as hereinafter described.

The filler 50 is preferably selected from a material wettable by, and inert to blood, having open pores therein sufficiently small in diameter as to provide for a capillary draw on blood deposited within the pores by the cannula. As used herein, "capillary draw" or "capillary effect" refers to the phenomena in which the free surface of the collected liquid, because of surface tension, will move through the confining environment and thus draw in more liquid until a head of liquid is achieved in which gravity prevents further increase in liquid volume, or until the source of liquid is removed. Generally, to achieve this effect such pore diameters should be no greater than about 0.254 millimeters. Best results are achieved if the average pore diameter is about 0.102 millimeters. The filler can be a rigid, self-sustaining material, or it can be collapsible.

In all cases, it is preferred that the filler initially extend from a location adjacent to closure means 38 in end portion 34, to a termination surface S removed from that closure means, which surface is beyond the extent of reach of the apertured tip 13 of cannula 11 and therefore beyond the delivery point of the blood. The filler retains this position due to its packing within the compartment, i.e., due to its compressive force. This construction insures that the filler surrounds the cannula tip 13 when it is inserted, so that delivered blood is contacted by capillary pores as soon as the blood is deposited by the cannula. The capillary effect of the pores serves to draw out the blood from the cannula. Further, it is preferred that such termination surface, after phase separation, be within the cell phase so as not to interfere with the removal of serum. Because of these preferences, the filler preferably extends as shown in FIG. 2 to more than 50% of the volume of tube 12 between septums 38, only if the filler is collapsible.

If it is not known what predetermined length of cannula is apt to be used with the device of the invention, the termination surface S can be conveniently located at a point which is removed from septum 38 a distance that is at least 50% of the length of the compartment. For noncollapsible fillers, it would be no more than 50%, to insure that the filler is located outside of the serum phase after centrifuging.

To collect a sufficient amount of blood, the void volume of the filler preferably is at least about 70% of its total volume.

To provide the above properties and preferred configurations, a variety of wettable materials can be used. Highly preferred examples include fibrous strands, such as glass or cotton fibers of any convenient length, and foamed, porous materials, such as polypropylene and polyethylene plastics. In the case of fibers, the pores comprise the space between the interwoven fibers. In the case of foamed plastics, it is the space in the cells.

Figure 3:
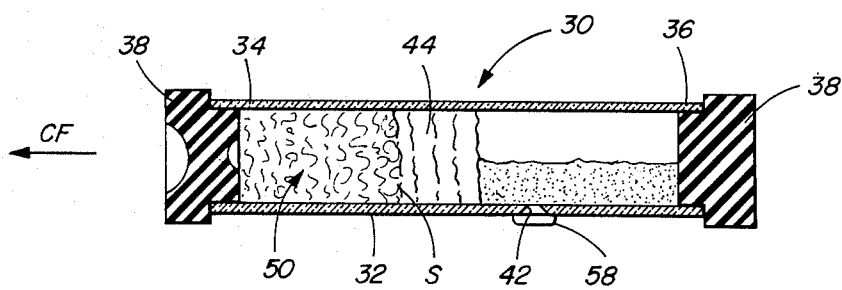
FIG. 3 is a view similar to that of FIG. 2, but illustrating the device after serum separation has been achieved by centrifuging.

After collecting venous blood from a vein V as shown in FIG. 2, device 30 is removed from syringe 12 and aperture 42 is closed, as by means of a self-adhering tape 58, FIG. 3. At this point filler 50 is completely saturated by blood (not shown). There is no leakage from aperture 42 prior to the application of tape 58, since the capillary effect retains the blood within the filler and the aperture 42 is not in contact with the filler. Phase separation is achieved by centrifuging the device along its axis 33 with a force generally exceeding about 1100 g's exerted from end portion 36 to end portion 34. Due to the heavier specific gravity of blood cells, they collect in portion 34. By selecting a material for collapsible filler 50 which has a specific gravity greater than or equal to about 1.1, it too ends up in the cell-collecting portion after centrifuging is complete, FIG. 3, with surface S being sufficiently withdrawn as to not extend into the collected serum. As used herein, "specific gravity" is measured with respect to the material of the filler in solid form, i.e., the void volume is not included in the calculations.

Also during phase separation, phase separator 44 by reason of its specific gravity moves under the steady influence of the centrifugal force from end portion 36 to the phase boundary of the serum and cells, where it seals as shown in FIG. 3 against any further fluid flow through tube 16. Thereafter, by removing or otherwise bypassing the septum in end portion 36, the serum can be poured off for further testing. Once collapsed, the filler will stay in the cell-collecting portion unless it has a fairly high spring constant. For materials with low spring constants, and thus a low compressive force tending to force the filler back to its original configuration, the displaced phase separator is sufficient to hold the filler in place, FIG. 3.

In the event filler 50 is a rigid, noncollapsible material, surface S must initially fall closer to end portion 34 than end portion 36 as noted above. In this case, the filler is over-saturated with blood to the extent of almost filling the entire compartment between septums 38 with such blood. In such instances, phase separator 44 also serves the function of blocking the septum in end portion 36 from "blood ring contamination", because the separator is sealed to the walls of tube 32 around its entire perimeter.

Any suitable material can be used for tube 32, although it will be readily apparent that, because of the simple construction, glass and rigid polymeric materials are particularly useful.

FIG. 4 illustrates an embodiment similar to that of FIG. 2, except that a driver-retainer is selected to cooperate with a collapsible filler having a specific gravity which can be less than 1.1, and/or having a relatively high spring constant. Parts similar to those previously described bear the same reference numeral to which the distinguishing suffix a is attached. Thus, tube 32a has filler 50a positioned at end portion 34a and phase separator 44a in position at end portion 36a, adjacent to septum 38a. In this case, however, a driver-retainer 59 is inserted between filler 50a and separator 44a, having a specific gravity which is greater than or equal to about 1.1. Synthetic or natural, rigid or flexible polymers are typical of materials useful as drivers, provided of course that they are inert to blood and its constituents. The driver can have any convenient shape, as long as it will permit fluid flow around it. Conveniently, this is achieved by a cylindrical form with a diameter less than the internal diameter or dimensions of tube 32a. To help hold the driver in position before and after centrifuging, projections 60 are spaced around the circumference of the driver and project a sufficient distance outwardly to frictionally engage selected portions only of the wall of tube 32a. These projections are particularly desirable if the filler has a relatively high spring constant such as would push the collapsed filler out through the gel instead of remaining confined as shown in FIG. 3. The driver-retainer prevents this from happening as it moves with the surfce S during centrifuging. The frictional engagement of the projections is insufficient, however, to prevent translation of the driver during centrifuging. The effect is that, upon centrifuging, driver-retainer 59 and and the filler move soley into end portion 34a, with termination surface S removed from the serum collected at end portion 36a.

Alternatively, if driver-retainer 59 is secured to surface S, filler 50a can have a specific gravity greater than or equal to about 1.1 with the driver having a specific gravity less than 1.1. The filler then pulls the retainer with it.

In FIGS. 5 and 6, the device as shown in the previous embodiments has been modified to include a dispenser, shown in FIG. 10 in position ready to dispense separated serum. Such a dispenser is only representative of a variety that can be used with the collection and separation device. Parts similar to those previously described bear the same reference numeral, to which is added the distinguishing suffix b. Thus, tube 32b is the same as described heretofore, except that end portion 36b is modified in the manner disclosed in the aforesaid application entitled "Telescoping Serum Separator and Dispenser". That is, a dispenser is included comprising a cavity 64 caused by a flared enlargement 65 of the tube compartment at end portion 36b, and a container 66 which telescopes over end portion 36b. Such container 66 comprises an end wall 72 having an interior side or surface 74 and an exterior side or surface 76, and opposed side walls 78 extending from side 74, terminating at an end 80 of the container 66 opposite to end wall 72. The side walls 78 accommodate or encompass an exterior surface 81 of the tube 32b, so that end portion 36b is movably mounted and specifically telescoped within end 80 of container 66. Preferably, the opposed walls 78 are arranged about an axis which is coincident with axis 33b. Thus, as with tube 32b, the walls 38 can have a shape in which the walls form one continuous wall.

The walls 78 have an interior surface 82 and an exterior surface 83. The interior surface 82 can be cylindrical while the exterior surface 83 can be either rectilinear or cylindrical. The interior of container 66 is temporarily blocked from fluid flow of serum from end 36b by virtue of the removable seal formed by side 74 of end wall 72 positioned against end surface 85, when container 66 is slid into its closed position, FIG. 5. Interior surface 82 is further provided with means for seating the container 66 on tube 32b before end 36b is unblocked as shown in FIG. 6, and for slidably moving the container 66 to the unblocked position. The means permitting the movement of container 66 to the two positions is the approximate coincidence of the interior diameter of surface 82 of container 66 and the exterior diameter of the walls of tube 32b, and the flexibility of walls 78. To seat container 66 when in the blocking position, FIG. 5, a sealing groove 84 is provided extending around the entire circumference of end portion 36b, shaped to mate with a rim or shoulder 86 of end 80. If desired, an O-ring, not shown, can be seated within the groove 84 to assist in the sealing. A similar sealing groove, not shown, can be formed in surface 81 to fit rim 86 when the container 66 is slid into the dispensing position, FIG. 6.

Preferably, two apertures 90 and 110 are formed in portions 92 and 112, respectively, of the side walls 78 for the dispensing operation depicted in FIG. 5. These apertures preferably are constructed in the manner disclosed in the aforesaid application entitled "Telescoping Serum Separator & Dispenser". Specifically, the portion 92 of the side wall 78 has a specially-constructed drop-forming platform 94 isolated from the rest of the exterior surface 83 by a connecting portion or surface 96, and surrounded by a protruding, protection shoulder 97. Aperture 90 has an exit portion which is centered within the platform 94 and an entrance portion in the interior surface 82 of portion 92.

The function of the platform 94 and aperture 90 is to accurately form successive drops of predictable, uniform volume, each of which is to be touched off on a suitable substrate. To provide this function with a fluid having such drastically varying properties as blood serum, certain features have been found to be useful. As disclosed in *Research Disclosure*, Vol. 133, May, 1975, Publication No. 13360, there preferably is a vertical separation of the platform 94 from the surface 83 by a distance $h$, FIG. 6, and a horizontal separation from shoulder 97 by a minimum width. Both of these preferably are such as to prevent a drop of blood serum from spreading from the platform to the remaining wall portions prior to drop transfer. Such drop spreading would interfere with accurate drop transfer. It has been found that a suitable value for the height $h$ is about 0.127 cm, while the separation of the platform from shoulder 97 should be at least about 0.05 cm, and preferably about 0.127 cm. Furthermore, the surface of the walls immediately adjacent to platform 94, that is the connecting surface 96, preferably slopes away from a line along which the force of gravity acts when the drop is formed, by an angle $\alpha$ which is between about 0° and about 15°. Negative angles are also usable. Any slope greater than this will encourage the drop to climb up and contact exterior surface 83, thus interfering with the proper drop size and drop removal.

To further insure that blood serum of the types commonly received from patients are properly dispensed as a drop from platform 54, in accurate micro-amounts, additional properties are desirable, and are described in the aforesaid *Research Disclosure* which is expressly incorporated herein by reference.

The effect of such features is to confine the drop dispensed from the container 66 to the surface of the platform 94. It will be appreciated that the entire surface of the platform 94 is contacted by the drop, and because the drop naturally assumes a quasi-spherical form, the contacted surface area of the platform will range from about 0.0026 sq. cm. for a 1 μl drop, to about 0.018 sq. cm. for a 30 μl drop. This represents a range in platform diameter, between the exterior edges thereof, which is between about 0.05 cm and about 0.15 cm. Alternatively, the surface area supporting, and in contact with, the drop can be increased for a given drop volume and platform diameter by either 1) forming a downwardly projecting rim for confining the drop, 2) making the platform surface concave, or 3) roughening the surface of platform 94.

All of the above features can be obtained by forming the container 66 out of copolymers such as acrylonitrile-butadiene-styrene (ABS), and polymers such as poly(acetal), poly(propylene), poly(styrene), high density poly(ethylene), and polyesters.

Aperture 110 in portion 112 of side walls 38 is preferably positioned opposite the aperture 90, and need otherwise be constructed only as a passageway for pressurized gas generated exterior to the container.

In this embodiment, the vent aperture for venting the device during blood collection comprises aperture 120 and a passageway 122 in end portion 36b extending from the flare enlargement 65 of cavity 64 to the exterior surface 81 of end portion 36b. When container 66 is in its blocking position with end wall surface 74 pressed against end surface 85, FIG. 5, aperture 120 is aligned with passageway 122 to provide a vent to the atmosphere. However, after centrifuging, the gel of separator 44b plugs passageway 120, FIG. 6, insuring that container 66 is a closed container for the pressurized dispensing step. A special constriction 128 in the passageway reduces the dimensions sufficiently to trap the gel within the passageway. Typically, the opening at constriction 128 should not exceed about 0.3 mm.

The dispensing operation is achieved after the centrifugal separation of the serum. Prior to centrifuging, separator 44 is confined within cavity 64 and against surface 74 of end wall 72, FIG. 5. After centrifuging, it has moved as shown in FIG. 6 to the serum-cell interface. The complete dispensing chamber ready for dispensing is formed by sliding the container 66 so that end wall 72 no longer blocks end portion 36b of tube 32b and rim 86 is moved out of groove 84. The serum is then free to flow into the dispensing chamber and into aperture 90. The dispensing chamber now comprises, in this expanded position, the end wall 72, side walls 78, the gel 44b sealing off the cell-portion of the blood and passageway 122, and the side walls of the serum-collecting portion of tube 32b, including end portion 36b. A suitable pressurizing means, not shown, such as an air hose, can be used to generate the pressure.

To insure that proper drop formation of predictable volume occurs the first time for a given pressure increase, the total air volume above the serum surface should be minimized. Such a feature can be particularly significant where, as here, the air volume is increased drastically before dispensing can be achieved. It has been found that when the air volume above the serum in the dispensing chamber opened to the extended position is about 1300 μl, for example, no problem occurs in accurate dispensing.

The invention has been described in detail with particular reference to certain preferred embodiments thereof, but it will be understood that variations and modifications can be effected within the spirit and scope of the invention.

What is claimed is:

1. A blood collection and separation device for use with a blood-delivering cannula having a penetrating portion extending a predetermined penetrating length to an apertured tip, said device comprising
    an elongated compartment having opposite end portions, one of which is for confining separated cells and the other of which is for confining separated serum;
    closure means in at least said one end portion for admitting a cannula and for closing the compartment;
    a vent aperture extending to the exterior of the device at said other end portion; and
    a microporous filler confined within said compartment, said filler
    1. filling said compartment at at least the point occupied by the cannula tip when inserted through said closure means,
    2. being wettable by and inert to blood, and
    3. being provided with open pores sufficiently small in diameter as to provide a capillary draw on blood deposited therein by the cannula.

2. A device as defined in claim 1, and further including within said compartment at said other end portion means for maintaining a phase separation between the blood serum and cells achieved by a centrifugal force sufficient to cause said phase separation.

3. A device as defined in claim 1, wherein said filler is collapsible when centrifuged at a force of at least about 1100 g's, and wherein said filler after centrifuging is located at said one end portion so as to occupy less than or equal to about half the length of the compartment.

4. The device as defined in claim 3, wherein the specific gravity of said filler is greater than or equal to about 1.1.

5. The device as defined in claim 3, and further including a movable driving member located within said compartment exterior of said filler, said member having a specific gravity greater than or equal to about 1.1.

6. The device as defined in claim 1, wherein said filler is relatively rigid and does not significantly collapse when centrifuged at a force of at least about 1100 g's, and is located at said one end portion so as to occupy less than or equal to about half the length of said compartment.

7. The device as defined in claim 1, wherein said filler is a fibrous material.

8. The device as defined in claim 1, and further including a dispensing chamber extending from said other end portion, and means for temporarily blocking liquid flow to said chamber until after phase separation, whereby said device is capable of dispensing serum separated in the device.

9. A vented liquid collection device for use with a liquid injector having a penetrating portion extending a predetermined penetrating length to an apertured tip, said device comprising an elongated compartment having opposite end portions, one of said end portions having a vent aperture extending to the exterior of the device, closure means in at least the other of said end portions for admitting a liquid injector and for closing the compartment; and a microporous filler confined within said compartment, said filler 1. filling said compartment at at least the point occupied by the apertured tip when inserted through said closure means,
2. being wettable by and inert to the liquid to be collected, and
3. being provided with open pores sufficiently small in diameter as to provide a capillary draw on liquid deposited therein by the injector.

10. An elongated compartment having opposite end portions, with a blood-delivering cannula having a penetrating portion extending a predetermined penetrating length to an apertured tip, said device comprising an elongated compartment having opposite end portions, one of which is for confining separated cells and the other of which is for confining separated serum;

closure means in at least said one end portion for admitting a cannula and for closing the compartment;

a vent aperture extending to the exterior of the device at said other end portion; and a microporous filler confined within said compartment extending from a position adjacent to said closure means to a point removed from said means a distance greater than said predetermined length, said filler being wettable by and inert to blood and being provided with open pores sufficiently small in diameter as to provide a capillary draw on blood deposited therein by the cannula.

11. A device as defined in claim 10, and further including within said compartment at said other end portion means for maintaining a phase separation between the blood serum and cells achieved by a centrifugal force sufficient to cause said phase separation.

12. A device as defined in claim 10, wherein said filler is collapsible when centrifuged at a force of at least about 1100 g's, and wherein said filler after centrifuging is located at said one end portion so as to occupy less than or equal to about half the length of the compartment.

13. The device as defined in claim 12, wherein the specific gravity of said filler is greater than or equal to about 1.1.

14. The device as defined in claim 12, and further including a movable driving member located within said compartment exterior of said filler, said member having a specific gravity greater than or equal to about 1.1.

15. The device as defined in claim 1, wherein said filler is relatively rigid and does not significantly collapse when centrifuged at a force of at least about 1100 g's, and is located at said one end portion so as to occupy less than or equal to about half the length of said compartment.

16. The device as defined in claim 10, wherein said filler is a fibrous material.

17. A device as defined in claim 10, and further including a dispensing chamber extending from said other end portion, and means for temporarily blocking liquid flow to said chamber until after phase separation, whereby said device is capable of dispensing serum separated in the device.

18. A blood collection and separation device, comprising a syringe having a tube open at one end and closed at the other and a cannula fixed to said closed end with a portion extending into said tube a predetermined length, said portion being apertured at its end proximal to said tube open end, an elongated compartment slidable within said tube and having opposite end portions, one end portion being adapted to confine separated blood cells and the other end portion being adapted to confine separated serum;

closure means in at least said one end portion for admitting said cannula into said compartment and for otherwise closing said compartment;

a vent aperture extending to the exterior of said compartment at said other end portion; and a microporous filler confined within said compartment and extending from a position adjacent to said closure means to a point removed from said means a distance greater than said predetermined length, said filler being wettable by and inert to blood and being provided with open pores sufficiently small in diameter as to provide a capillary draw on blood deposited therein by the cannula.

19. A blood collection and separation device for use with a blood-delivering cannula having a penetration portion extending a predetermined penetrating length to an apertured tip, said device comprising an elongated compartment having opposite end portions, one of which is for confining separated cells and the other of which is for confining separated serum;

closure means in at least said one end portion for admitting a cannula and for closing the compartment;

a vent aperture extending to the exterior of the device at said other end portion; and a microporous filler confined within said compartment extending from a position adjacent to said closure means a distance of at least about one-half the length of said compartment, said filler being wettable by and inert to blood and being provided with open pores sufficiently small in diameter as to provide a capillary draw on blood deposited therein by the cannula.

* * * * *